US00PP31569P2

(12) United States Plant Patent
Hartman

(10) Patent No.: US PP31,569 P2
(45) Date of Patent: Mar. 17, 2020

(54) ***CALADIUM* PLANT NAMED 'ZRD 2318-183'**

(50) Latin Name: ***Caladium* X *hortulanum***
Varietal Denomination: ZRD 2318-183

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 16/501,047

(22) Filed: Feb. 13, 2019

(51) Int. Cl.
*A01H 5/02* (2018.01)
*A01H 6/10* (2018.01)

(52) U.S. Cl.
USPC ..... Plt./373
CPC ..... *A01H 6/10* (2018.05)

(58) Field of Classification Search
USPC ..... Plt./373
CPC ..... A01H 6/10; A01H 5/02
See application file for complete search history.

*Primary Examiner* — Keith O. Robinson
(74) *Attorney, Agent, or Firm* — C. A. Whealy

(57) ABSTRACT

A new and distinct cultivar of *Caladium* plant named 'ZRD 2318-183', characterized by its intermediate to tall height; mounding habit; dense and bushy appearance; vigorous growth habit and rapid growth rate; fancy-type leaves that are dark green in color with bright white-colored venation surrounded with bright white-colored areas and interveinal areas that are bright white and greyed green in color with white-colored flecks, speckles, blotches and streaks; and leaf petioles that are black in color with green and white-colored stripes, stipples and streaks.

4 Drawing Sheets

Botanical designation: *Caladium* X *hortulanum*.
Cultivar denomination: 'ZRD 2318-183'.

BACKGROUND OF THE INVENTION

The present invention relates to a new and distinct cultivar of *Caladium* plant, botanically known as *Caladium* X *hortulanum*, commercially referred to as a fancy leaf-type *Caladium* and hereinafter referred to by the name 'ZRD 2318-183'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2009 in Avon Park, Fla. of *Caladium* X *hortulanum* 'White Christmas', not patented, as the female, or seed, parent with *Caladium* X *hortulanum* 'Aaron', not patented, as the male, or pollen, parent. The new *Caladium* plant was discovered and selected by the Inventor as a single plant within the progeny of the stated cross-pollination in a controlled outdoor nursery environment in Zolfo Springs, Fla. in September, 2010.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Fla. since April, 2011 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'ZRD 2318-183'. These characteristics in combination distinguish 'ZRD 2318-183' as a new and distinct *Caladium* plant:

1. Intermediate to tall in height and mounding habit; dense and bushy appearance.
2. Vigorous growth habit and rapid growth rate.
3. Fancy-type leaves that are dark green in color with bright white-colored venation surrounded with bright white-colored areas and interveinal areas that are bright white and greyed green in color with white-colored flecks, speckles, blotches and streaks.
4. Leaf petioles that are black in color with green and white-colored stripes, stipples and streaks.

Plants of the new *Caladium* differ primarily from plants of the female parent, 'White Christmas', in the following characteristics:

1. Leaves of plants of the new *Caladium* are flatter than and not as rugose as leaves of 'White Christmas'.
2. Plants of the new *Caladium* and 'White Christmas' differ in leaf color as leaves of plants of the new *Caladium* are dark green in color with bright white-colored venation surrounded with bright white-colored areas and interveinal areas that are bright white and greyed green in color with white-colored flecks, speckles, blotches and streaks whereas leaves of plants of 'White Christmas' have distinct dark green-colored venation with white-colored interveinal areas that are often tinged with pink and dark green-colored borders.
3. Plants of the new *Caladium* and 'White Christmas' differ in leaf petiole color as leaf petioles of plants of the new *Caladium* are black in color with green and white-colored stripes, stipples and streaks whereas leaf petioles of 'White Christmas' are mostly green in color with black-colored stripes.

Plants of the new *Caladium* differ primarily from plants of the male parent, 'Aaron', in the following characteristics:

1. Plants of the new *Caladium* and 'Aaron' differ in leaf color as leaves of plants of the new *Caladium* are dark green in color with bright white-colored venation surrounded with bright white-colored areas and interveinal areas that are bright white and greyed green in color with white-colored flecks, speckles, blotches and streaks whereas leaves of plants of 'Aaron' have white-colored venation and radiating interveinal areas surrounded with green-colored borders.
2. Plants of the new *Caladium* and 'Aaron' differ in leaf petiole color as leaf petioles of plants of the new *Caladium* are black in color with green and white-colored stripes, stipples and streaks whereas leaf petioles of 'Aaron' are green in color.

Plants of the new *Caladium* can be compared to plants of *Caladium* X *hortulanum* 'White Cap', disclosed in U.S. Plant Pat. No. 23,815. In side-by-side comparisons, plants of the new *Caladium* differ primarily from plants of 'White Cap' in the following characteristics:

1. Plants of the new *Caladium* and 'White Cap' differ in leaf color as leaves of plants of the new *Caladium* are have more distinctive and brighter white-colored venal and interveinal areas than leaves of plants of 'White Cap'.
2. Plants of the new *Caladium* and 'White Cap' differ in leaf petiole color as leaf petioles of plants of the new *Caladium* are black in color with green and white-colored stripes, stipples and streaks whereas leaf petioles of 'White Cap' are mostly green in color.

Plants of the new *Caladium* can also be compared to plants of *Caladium* X *hortulanum* 'Candidum Senior', not patented. In side-by-side comparisons, plants of the new *Caladium* differ primarily from plants of 'Candidum Senior' in the following characteristics:

1. Leaves of plants of the new *Caladium* are flatter than and not as rugose as leaves of 'Candidum Senior'.
2. Plants of the new *Caladium* and 'Candidum Senior' differ in leaf color as leaves of plants of the new *Caladium* are dark green in color with bright white-colored venation surrounded with bright white-colored areas and interveinal areas that are bright white and greyed green in color with white-colored flecks, speckles, blotches and streaks whereas leaves of plants of 'Candidum Senior' are greenish white in color with medium green-colored venation and thin green-colored margins.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'ZRD 2318-183' in a container and grown in a shadehouse (tuber de-eyed).

The photograph at the top of the second sheet is a side perspective view of typical plants of 'ZRD 2318-183' grown in an open production field.

The photograph at the bottom of the second sheet is a comparison view of typical plants of 'ZRD 2318-183' grown in containers; the plant on the left has not had its tuber de-eyed and the plant on the right has had its tuber de-eyed prior to planting.

The photograph at the top of the third sheet is a comparison view of typical potted plants of the female parent, 'White Christmas' (left), 'ZRD 2318-183' (center) and the male parent, 'Aaron' (right).

The photograph at the bottom of the third sheet is a comparison view of typical potted plants of 'White Cap' (right), 'ZRD 2318-183' (center) and 'Candidum Senior' (left).

The photograph at the top of the fourth sheet is a close-up view of typical freshly-harvested tubers with roots and leaf petioles of 'ZRD 2318-183'.

The photograph at the bottom of the fourth sheet is a close-up view of a typical inflorescence of 'ZRD 2318-183'.

DETAILED BOTANICAL DESCRIPTION

The aforementioned photographs and following observations and measurements describe plants grown in 15-cm containers in a polypropylene-covered shadehouse (30% light reduction) in Avon Park, Fla. and plants grown in ground beds under full sunlight conditions in an outdoor nursery in Crewsville, Fla. The plants were grown under cultural practices typical of commercial shadehouse and outdoor nursery production. During the production of the shadehouse-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from 10,000 to 12,000 foot-candles. Plants grown in the shadehouse were eight weeks old and plants grown in the outdoor nursery were seven months old when the photographs and the detailed description were taken. In the following description, color references are made to The Royal Horticultural Society Colour Chart, 2001 Edition, except where general terms of ordinary dictionary significance are used.

Botanical classification: *Caladium* X *hortulanum* 'ZRD 2318-183'.

Parentage:

*Female, or seed, parent.*—*Caladium* X *hortulanum* 'White Christmas', not patented.

*Male, or pollen, parent.*—*Caladium* X *hortulanum* 'Aaron', not patented.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented; individual segments irregular to somewhat elliptic in shape. Height: About 3.4 cm to 3.8 cm. Diameter: About 7.2 cm to 12.1 cm. Segment height: About 2.9 cm. Segment diameter: About 4 cm. Axillary bud size: About 2.5 mm by 3.5 mm. Texture: Thick, starchy; somewhat brittle. Color: Epidermis, freshly-harvested: Close to 155D. Epidermis, dried: Close to 200A. Cortical tissue: Close to 10C and 4C to 4D. Axillary buds: Close to 36C. Root description: Thick, fleshy contractile roots with few lateral branches; color, close to N155D. Rooting habit: Medium density.

Plant description:

*Plant type*.—Herbaceous perennial; suitable as a potted plant in containers 15-cm to 25-cm and suitable as a landscape plant in shaded areas.

*Plant and growth habit*.—Intermediate to tall in height and mounded plant habit; inverted triangle and wider than tall; dense and bushy appearance; vigorous growth habit and rapid growth rate; potted plants finish in saleable form in about six to seven weeks after planting tubers; leaf petioles and leaves arise from one or more growing points on tubers; leaf petioles initially upright and leaning outwardly with development.

*Plant height, from soil level to top of foliar plane, shadehouse-grown potted plants*.—About 31 cm to 37 cm.

*Plant height, from soil level to top of inflorescences, shadehouse-grown potted plants*.—About 36 cm.

*Plant diameter or spread, shadehouse-grown potted plants*.—About 38 cm to 43 cm.

*Number of shoots per plant, shadehouse-grown potted plants, tubers not de-eyed*.—About four to six develop per #1 tuber.

*Number of shoots per plant, shadehouse-grown potted plants, tubers de-eyed*.—About four to eight develop per #1 tuber.

*Cataphylls, shadehouse-grown potted plants*.—Length: About 4.9 cm to 10 cm. Width: About 1.2 cm to 1.6 cm. Shape: Lanceolate to narrowly elliptic. Apex: Acuminate. Base: Sheathing the stem. Color, inner surface: Close to N155C; towards the apex and margins, sparsely streaked and stippled with 200A and 200B; colors and patterns on the outer surface are visible on the inner surface. Color, outer surface: Close to N155C streaked, stippled, striped and mottled with 200A and 200B tinged with 147A; with development, color becoming closer to 200A to 200B.

Leaf description:

*Arrangement and type*.—Alternate; simple; fancy-type.

*Length, shadehouse-grown potted plants*.—About 15.5 cm to 20 cm.

*Width, shadehouse-grown potted plants*.—About 11 cm to 16.5 cm.

*Shape*.—Ovate.

*Apex*.—Acute.

*Base*.—Sagittate to peltate.

*Margin*.—Entire; mostly flat with broad undulations.

*Texture and luster, upper surface*.—Mostly smooth to slightly rugose, glabrous; dull sheen.

*Texture and luster, lower surface*.—Smooth, glabous; slightly glaucous; dull sheen.

*Venation pattern*.—Pinnate.

*Color, shadehouse-grown potted plants*.—Developing and fully developed leaves, upper surface: Background: Close to 147A. Leaf edge: Close to 183A and 187A. Basal notch: Close to 187A. Midvein: Close to 157B to 157C with streaks, close to 195D; at the petiole attachment, close to 187C; areas surrounding venation, brighter white than 155C and "mosaic" of close to 155C, 147A, 147B and 191C. Primary venation: Close to 157B to 157C with flecks, close to 147B; occasionally flushed with close to 187B; areas surrounding venation, brighter white than 155C and "mosaic" of close to 155C, 147A, 147B and 191C. Interveinal areas: Random areas that are brighter white than 155C which may be flushed with 185D and close to 191C in color. Random flecks, speckles, blotches and streaks: Close to 155C. Developing and fully developed leaves, lower surface: Background: Close to 191A. Leaf edge: Close to 187A. Basal notch: Close to 187B. Midvein: Close to 145D and 155C, may be tinged with 49D and/or N199A; at the petiole attachment, close to 187D; areas surrounding venation, close to 155B and "mosaic" of close to 147B, 147C and 191A. Primary venation: Close to 145D and 155C; areas surrounding venation, close to 155B and "mosaic" of close to 147B, 147C and 191A. Interveinal areas: Random areas that are close to 155B, which may be flushed with 70D, and close to 147B and 147C. Random flecks, speckles, blotches and streaks: Close to 191A.

*Petioles*.—Aspect: Initially upright and straight and outwardly leaning with development; flexible. Length, shadehouse-grown potted plants: About 23 cm to 30.1 cm. Diameter, distally, shadehouse-grown potted plants: About 4 mm to 5 mm. Diameter, proximally, shadehouse-grown potted plants: About 7 mm to 10 mm. Texture and luster: Smooth, glabrous; glaucous; dull. Color, shadehouse-grown potted plants, when developing and fully developed: Proximally, close to 202A variably striped, stippled and streaked with close to 147D and N155D; distally (just below leaf junction), close to 147D variably striped, stippled and streaked with close to 202A. Wing length, shadehouse-grown potted plants: About 6.5 cm to 8.5 cm. Wing diameter, shadehouse-grown potted plants: About 8 mm to 9 mm. Texture and luster, inner and outer surfaces: Smooth, glabrous; dull. Wing color, shadehouse-grown potted plants: Inner surface: Close to N155C; distally, sparsely streaked and stippled with 200A and 200B; colors and patterns on the outer surface are visible on the inner surface. Outer surface: Close to 202A marbled and stippled with 147A; distally, close to 196D tinged with 147C.

Inflorescence description: Inflorescences observed on nine week-old shadehouse-grown potted plants.

*Inflorescence arrangement*.—Upright hooded spathes surrounding a columnar spadix borne on an upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; jasmine-like with mint and camphor notes.

*Natural flowering season and flower longevity*.—Plants of the new *Caladium* typically flower during the spring and summer in central Florida; flowers develop about nine weeks after growth commences; inflorescences last about three days before fading; inflorescences persistent.

*Spathe*.—Length, overall: About 8.7 cm. Length, distal open portion: About 5 cm. Length, proximal closed portion: About 3.7 cm. Width, distal open portion: About 2.8 cm. Depth, distal open portion: About 2.5 cm. Width, at constriction: About 1.2 cm. Width, proximal closed portion: About 2.3 cm. Shape, open portion: Elliptic. Apex: Acuminate. Base: Acute. Margin: Entire; smooth. Texture and luster, front surface: Smooth, glabrous; dull. Texture and luster, rear surface: Smooth, glabrous; dull; proximally, slightly glaucous. Color, front surface: Distal open portion: Close to 155C; towards the margins, variably tinged with 145D; with development, color becoming closer to 200C and 200D. Proximal closed portion: Close to 147D; proximally, faintly tinged with 187A; color does not change with development. Color, rear surface: Distal open portion: Close to 145C and 145D marbled with brighter white than 155C; color does not change with development. Proximal closed portion: Close to 147B and 147C; towards the margins, mottled with 145C and 145D; color does not change with development.

*Spadix*.—Length, overall: About 6.5 cm. Length, male flower zone: About 3.3 cm. Length, sterile zone: About 1.5 cm. Length, female flower zone: About 1.7 cm. Diameter, male flower zone: About 8.5 mm. Diameter, sterile flower zone: About 5 mm. Diameter, female flower zone: About 1 cm. Shape: Columnar to spindle-shaped. Apex: Acute. Base: Obtuse. Aspect: Upright. Color, mature, male zone: Close to 158C. Color, mature, sterile zone: Close to 158C. Color, mature, female zone: Close to 155B. Male flowers: Quantity per spadix: About 120. Shape: Obovate. Height: About 3 mm. Diameter: About 3 mm. Pollen amount: Abundant. Pollen color: Close to 4C. Female flowers: Quantity per spadix: About 165. Shape: Obovate. Height: About 2.5 mm. Diameter: About 2.5 mm. Stigma color: Close to 155B. Ovary color: Close to 8D.

*Scape*.—Length: About 27.3 cm. Diameter: About 6 mm. Strength: Sturdy; somewhat flexible. Aspect: Mostly erect. Texture and luster: Smooth, glabrous; dull; distally, slightly glaucous. Color: Close to 147B to 147C and 199D striped, streaked and stippled with 202A, 200A and 200B; distally, close to 147B to 147C striped, streaked and stippled with 202A, 200A and 200B.

*Seeds and fruits*.—To date, seed and fruit development have not been observed on plants of the new *Caladium*.

Pathogen & pest tolerance: Plants of the new *Caladium* have been observed to have average tolerance to *Pythium* Root Rot and above average tolerance to *Xanthomonas* Leaf Spot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'ZRD 2318-183' as illustrated and described.

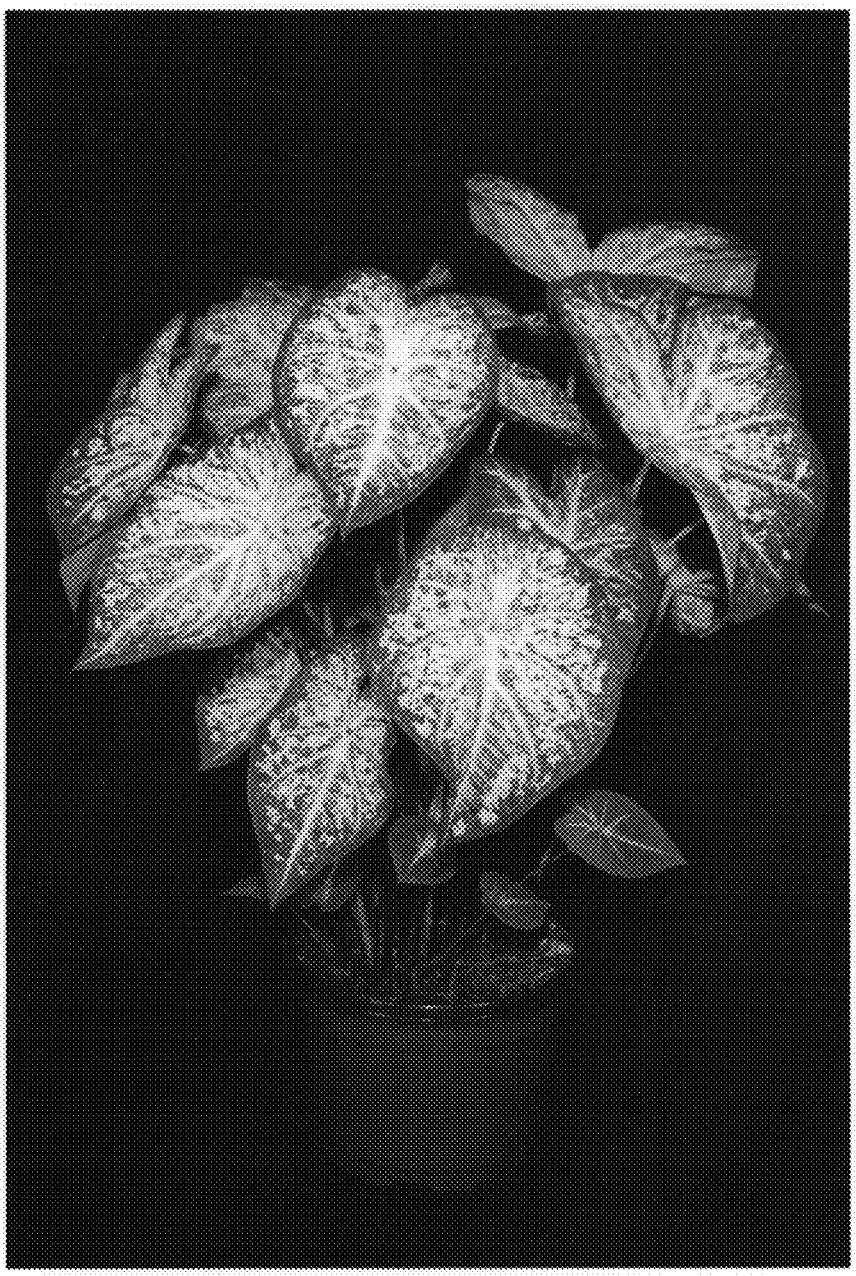

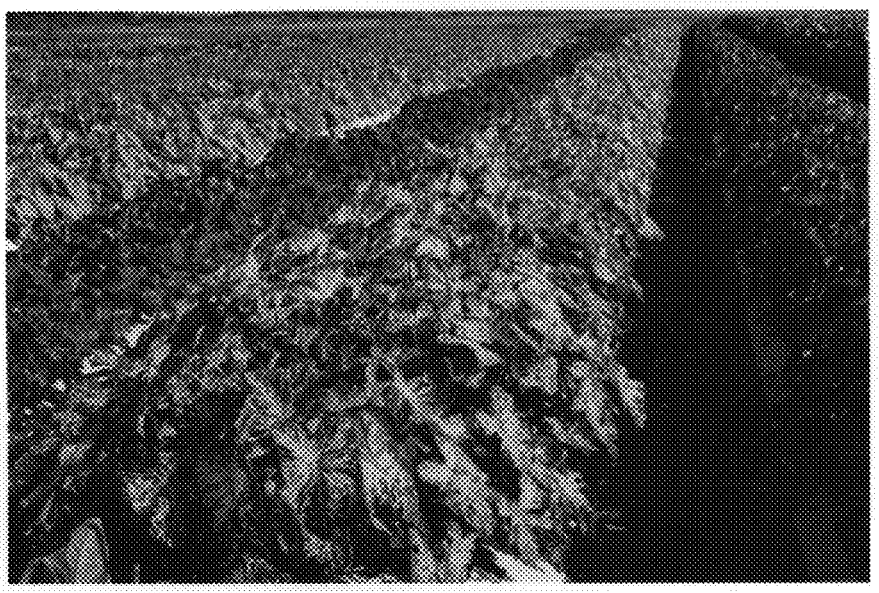
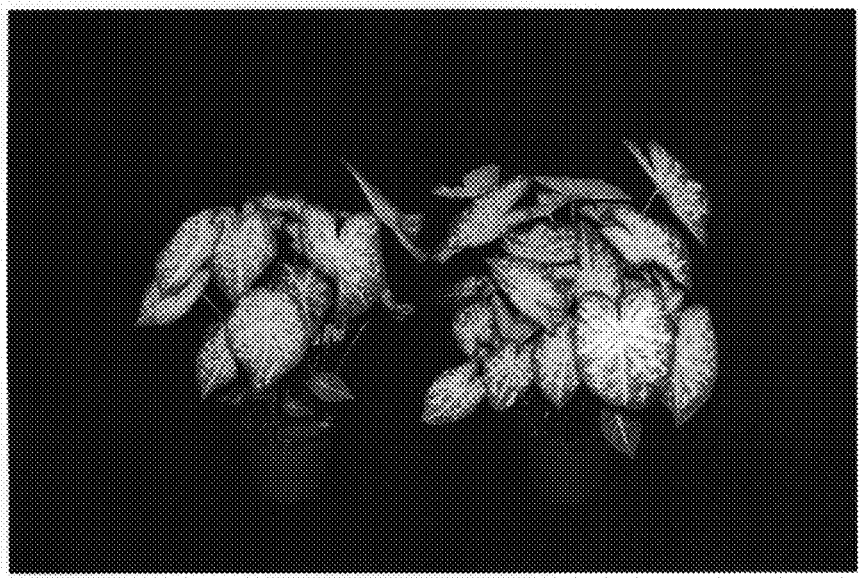

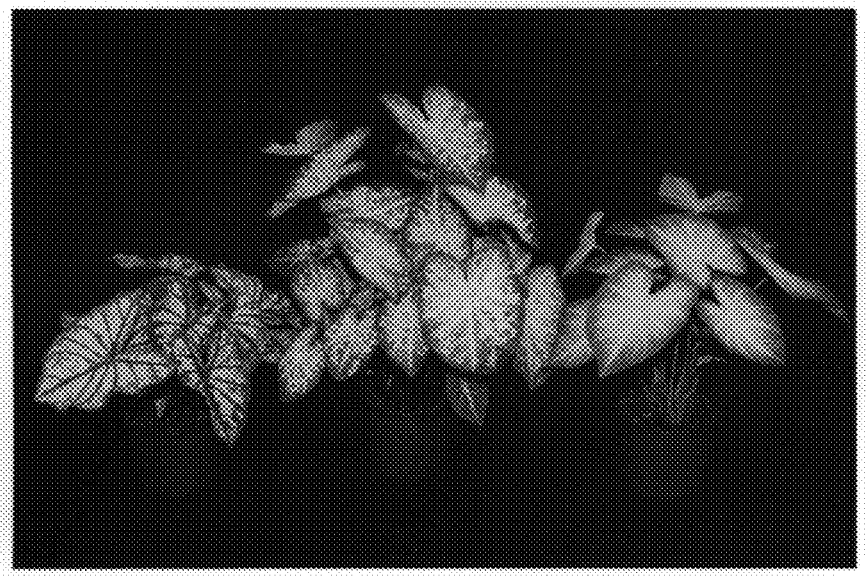
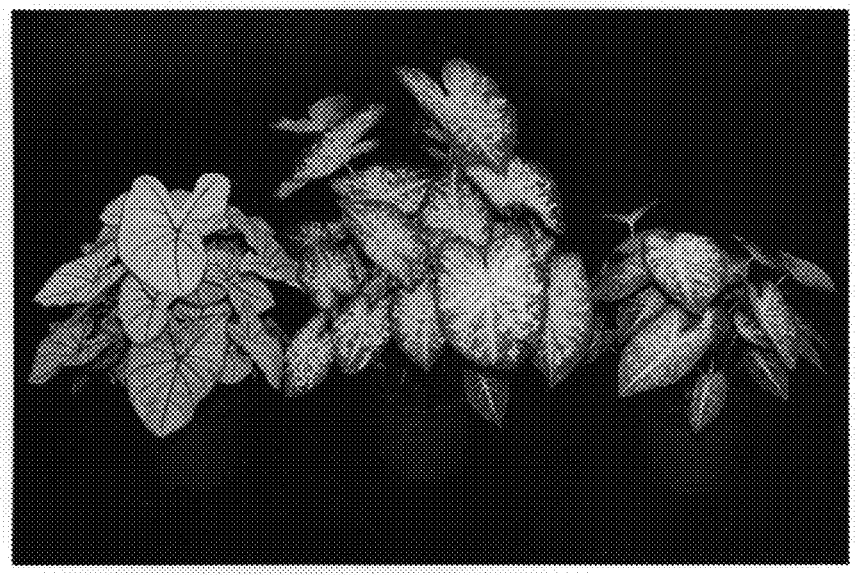

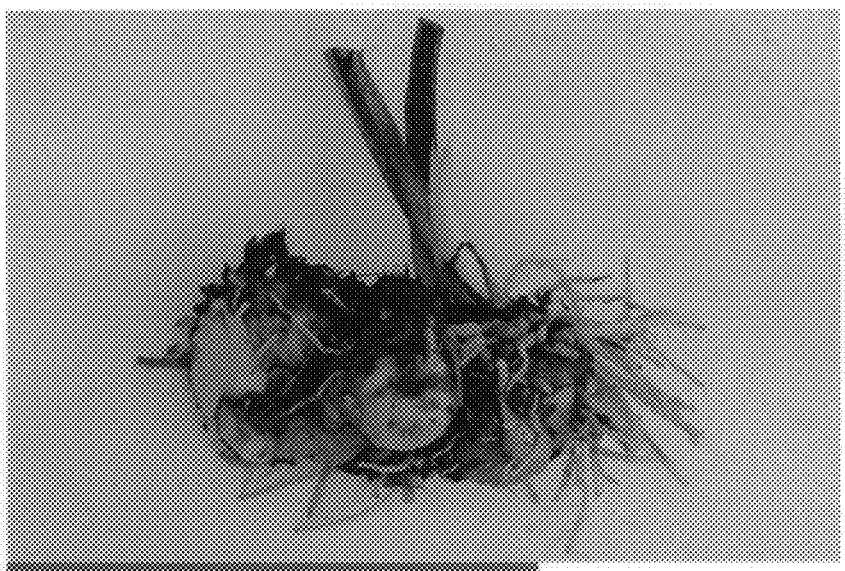
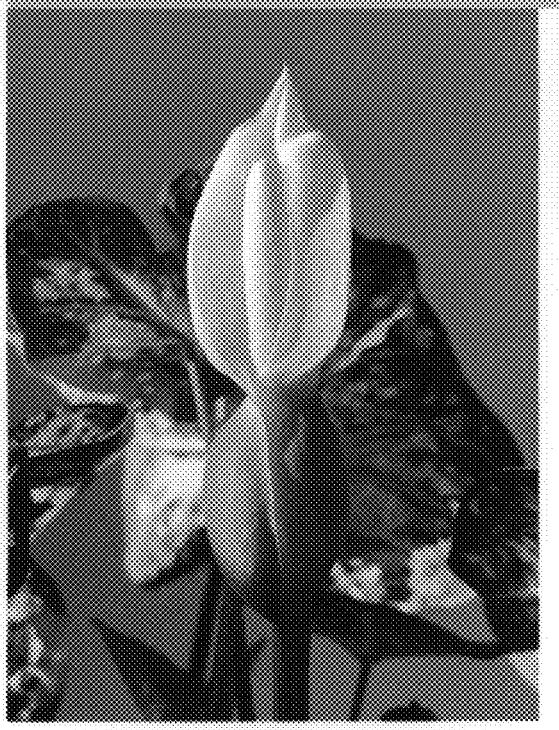

* * * * *